(12) United States Patent
Lee et al.

(10) Patent No.: US 11,510,580 B2
(45) Date of Patent: Nov. 29, 2022

(54) TOUCH PEN, ELECTRONIC DEVICE, AND APPARATUS AND METHOD FOR MEASURING BIO-INFORMATION

(71) Applicant: SAMSUNG ELECTRONICS CO., LTD., Suwon-si (KR)

(72) Inventors: Jong Wook Lee, Suwon-si (KR); Byung Hoon Ko, Hwaseong-si (KR); Young Soo Kim, Seoul (KR); Chang Mok Choi, Suwon-si (KR); Jeong Eun Hwang, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 446 days.

(21) Appl. No.: 16/812,939

(22) Filed: Mar. 9, 2020

(65) Prior Publication Data

US 2021/0022622 A1 Jan. 28, 2021

(30) Foreign Application Priority Data

Jul. 24, 2019 (KR) ........................ 10-2019-0089715

(51) Int. Cl.
*A61B 5/021* (2006.01)
*A61B 5/1455* (2006.01)
(Continued)

(52) U.S. Cl.
CPC ...... *A61B 5/02108* (2013.01); *A61B 5/02141* (2013.01); *A61B 5/02427* (2013.01);
(Continued)

(58) Field of Classification Search
CPC ......... A61B 5/02; A61B 5/0205; A61B 5/021; A61B 5/02108; A61B 5/02116; A61B 5/02141; A61B 5/02241; A61B 5/024; A61B 5/02416; A61B 5/02427; A61B 5/02433; A61B 5/1455; A61B 5/14551;
(Continued)

(56) References Cited

U.S. PATENT DOCUMENTS 8,761,853 B2* 6/2014 Thaveeprungsriporn ....................
A61B 5/6898
600/323
9,770,177 B2 9/2017 Lee et al.
(Continued)

FOREIGN PATENT DOCUMENTS

JP 2006-102163 A 4/2006
KR 10-2010-0042566 A 4/2010
(Continued)

*Primary Examiner* — Chu Chuan Liu
(74) *Attorney, Agent, or Firm* — Sughrue Mion, PLLC

(57) ABSTRACT

An electronic device according to an aspect of the present disclosure includes a touch screen. The electronic device includes a communication interface that may receive, from a touch pen, a pulse wave signal of a user which is measured from a finger of the user by the touch pen while the touch pen is placed on the touch screen. The electronic device includes a processor that may determine whether a measurement posture of the user is appropriate based on whether the finger touches the touch screen, and in response to determining that the user's measurement posture is appropriate, estimate bio-information of the user based on the received pulse wave signal.

20 Claims, 17 Drawing Sheets

(51) Int. Cl.
*A61B 5/00* (2006.01)
*G06F 3/0354* (2013.01)
*G06F 3/01* (2006.01)
*A61B 5/024* (2006.01)

(52) U.S. Cl.
CPC .......... *A61B 5/6897* (2013.01); *A61B 5/6898* (2013.01); *G06F 3/011* (2013.01); *G06F 3/03545* (2013.01)

(58) Field of Classification Search
CPC . A61B 5/14552; A61B 5/6826; A61B 5/6898; A61B 5/6897
See application file for complete search history.

(56) References Cited

U.S. PATENT DOCUMENTS

| | | | |
|---|---|---|---|
| 10,206,631 | B2 | 2/2019 | Gil et al. |
| 2009/0264713 | A1 | 10/2009 | Van Loenen et al. |
| 2015/0062078 | A1* | 3/2015 | Christman ........... A61B 5/6897 345/174 |
| 2015/0119654 | A1 | 4/2015 | Martin et al. |
| 2016/0213264 | A1 | 7/2016 | Gil et al. |
| 2016/0213324 | A1 | 7/2016 | Gil et al. |
| 2016/0213331 | A1 | 7/2016 | Gil et al. |
| 2017/0007136 | A1 | 1/2017 | Gil |
| 2017/0079591 | A1 | 3/2017 | Gruhlke et al. |
| 2017/0180988 | A1* | 6/2017 | Kim ..................... A61B 5/6887 |
| 2017/0251935 | A1 | 9/2017 | Yuen |
| 2017/0347899 | A1 | 12/2017 | Bhushan et al. |
| 2017/0367661 | A1 | 12/2017 | Gil et al. |
| 2018/0249918 | A1 | 9/2018 | Kirenko et al. |

FOREIGN PATENT DOCUMENTS

| | | |
|---|---|---|
| KR | 10-2012-0116331 A | 10/2012 |
| KR | 10-1638381 B1 | 7/2016 |
| KR | 10-2018-0065039 A | 6/2018 |
| WO | 2018150261 A2 | 8/2018 |
| WO | 2018172810 A1 | 9/2018 |

* cited by examiner

TOUCH PEN, ELECTRONIC DEVICE, AND APPARATUS AND METHOD FOR MEASURING BIO-INFORMATION

CROSS-REFERENCE TO RELATED APPLICATION(S)

This application is based on and claims priority under 35 U.S.C. § 119 to Korean Patent Application No. 10-2019-0089715, filed on Jul. 24, 2019, in the Korean Intellectual Property Office, the disclosure of which is incorporated by reference herein in its entirety.

BACKGROUND

1. Field

The disclosure relates to technology for cufflessly measuring blood pressure.

2. Description of Related Art

A pressurized cuff is generally used for measuring blood pressure. A blood pressure measuring method utilizing the pressurized cuff is a non-continuous measuring method, in which the cuff is inflated until the arterial pressure reaches a maximum value, and then the pressure in the cuff is slowly released. However, the pressurized cuff includes a pressure pump and the like, such that the cuff is unsuitable for use in association with a mobile device.

Recently, research has been conducted on blood pressure measuring apparatuses for cufflessly measuring blood pressure in a non-pressure-based manner without using a cuff, and examples thereof include a blood pressure measuring apparatus using Pulse Transit Time (PTT) and a blood pressure measuring apparatus using Pulse Wave Analysis (PWA). However, the blood pressure measuring apparatus using PTT is inconvenient in that correction is required for each user to ensure accuracy of measurement; and since bio-signals should be measured at two or more positions to measure the pulse wave velocity, the apparatus cannot be manufactured in a compact size. Further, the blood pressure measuring apparatus using PWA estimates blood pressure by analyzing only a pulse waveform, such that the PWA is vulnerable to noise, and blood pressure may not be measured accurately.

SUMMARY

Provided is an apparatus and method for cufflessly measuring blood pressure with improved accuracy by using a touch pen.

Additional aspects will be set forth in part in the description which follows and, in part, will be apparent from the description, or may be learned by practice of the presented embodiments.

According to an aspect of the disclosure, an electronic device may include a touch screen; a communication interface configured to receive, from a touch pen, a pulse wave signal of a user which is measured from a finger of the user by the touch pen while the touch pen is placed on the touch screen; and a processor configured to: determine whether a measurement posture of the user is appropriate based on whether the finger touches the touch screen; and in response to determining that the user's measurement posture is appropriate, estimate bio-information of the user based on the received pulse wave signal.

The processor is configured to, in response to the finger touching the touch screen, determine that the user's measurement posture is inappropriate.

The communication interface is configured to receive, from the touch pen, a force value of the finger pressing the touch pen while the touch pen is placed on the touch screen; and the processor is configured to estimate the user's bio-information based on the received force value and the pulse wave signal.

Based on the received force value, generate force guide information for guiding a force of the finger pressing the touch pen to be increased or decreased by the user while the touch pen measures the pulse wave signal; and provide the generated force guide information to the user.

The processor is configured to display a touch pen position guideline, indicating a position to place the touch pen, in a portion of the touch screen.

The communication interface is configured to receive, from the touch pen, an acceleration value of the touch pen which is measured while the touch pen is placed on the touch screen; and the processor is configured to determine whether the touch pen is moved based on the received acceleration value of the touch pen; and in response to determining that the touch pen is moved, generate a warning signal.

The electronic device may further include a force sensor configured to measure a pressing force of the finger pressing the touch pen while the touch pen is placed on the touch screen.

The pulse wave signal may be a Photoplethysmogram (PPG) signal.

The bio-information may be blood pressure.

According to an aspect of the disclosure, an apparatus for measuring bio-information may include a touch pen comprising a pulse wave sensor configured to, in response to a touch of a finger of a user while the touch pen is placed on a touch screen of an electronic device, measure a pulse wave signal of the user from the finger of the user; and a first communication interface configured to transmit the measured pulse wave signal to the electronic device; and the electronic device comprising a touch screen; a second communication interface configured to receive the pulse wave signal from the touch pen; and a processor configured to determine whether a measurement posture of the user is appropriate based on whether the finger touches the touch screen; and in response to determining that the user's measurement posture is appropriate, estimate bio-information of the user based on the received pulse wave signal.

The touch pen may further include a force sensor configured to measure a pressing force of the finger pressing the touch pen while the touch pen is placed on the touch screen of the electronic device.

The electronic device may further include a force sensor configured to measure a pressing force of the finger pressing the touch pen while the touch pen is placed on the touch screen of the electronic device.

The touch pen may further include an acceleration sensor configured to measure acceleration of the touch pen while the touch pen is placed on the touch screen of the electronic device.

The processor is configured to display a touch pen position guideline, indicating a position to place the touch pen, in a portion of the touch screen.

According to an aspect of the disclosure, a method of measuring bio-information by an electronic device having a touch screen may include receiving, from a touch pen, a pulse wave signal of a user which is measured from a finger of the user by the touch pen while the touch pen is placed on the touch screen; determining whether a measurement posture of the user is appropriate based on whether the finger of the user touches the touch screen; and in response to determining that the user's measurement posture is appropriate, estimating bio-information of the user based on the received pulse wave signal.

The determining whether the user's measurement posture is appropriate comprises, in response to the finger touching the touch screen, determining that the user's measurement posture is inappropriate.

The method may further include receiving, from the touch pen, a force value of the finger pressing the touch pen while the touch pen is placed on the touch screen; based on the received force value, generating force guide information for guiding a force of the finger pressing the touch pen to be increased or decreased by the user while the touch pen measures the pulse wave signal; and providing the generated force guide information to the user, wherein the estimating of the user's bio-information comprises estimating the user's bio-information based on the received force value and pulse wave signal.

The method may further include measuring a pressing force of the finger pressing the touch pen while the touch pen is placed on the touch screen; based on the received force value, generating force guide information for guiding a force of the finger pressing the touch pen to be increased or decreased by the user while the touch pen measures the pulse wave signal; and providing the generated force guide information to the user, wherein the estimating of the user's bio-information comprises estimating the user's bio-information based on the received force value and pulse wave signal.

The method may further include displaying a touch pen position guideline, indicating a position to place the touch pen, in a portion of the touch screen.

The method may further include receiving, from the touch pen, an acceleration value of the touch pen which is measured while the touch pen is placed on the touch screen; determining whether the touch pen is moved based on the received acceleration value of the touch pen; and in response to determining that the touch pen is moved, generating a warning signal.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
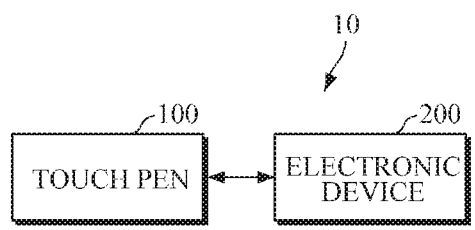
FIG. 1 is a block diagram illustrating an apparatus for measuring bio-information according to an embodiment.

Throughout the drawings and the detailed description, unless otherwise described, the same drawing reference numerals may refer to the same elements, features, and structures. The relative size and depiction of these elements, features, and structures may be exaggerated for clarity, illustration, and convenience.

DETAILED DESCRIPTION

Hereinafter, embodiments of the present disclosure will be described in detail with reference to the accompanying drawings. It should be noted that wherever possible, the same reference symbols may refer to same parts even in different drawings. In the following description, a detailed description of known functions and configurations incorporated herein may be omitted so as to not obscure the subject matter of the present disclosure.

Process steps described herein may be performed differently from a specified order, unless a specified order is clearly stated in the context of the disclosure. That is, each step may be performed in a specified order, at substantially the same time, in a different order, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although terms such as "first," "second," etc. may be used herein to describe various elements, these elements might not be limited by these terms. These terms may be used to distinguish one element from another. Any references to the singular form of a term may include the plural form of the term unless expressly stated otherwise. In the present specification, it should be understood that terms, such as "including," "having," etc., may indicate the existence of the features, numbers, steps, actions, components, parts, or combinations thereof, disclosed in the specification, and may not preclude the possibility that one or more other features, numbers, steps, actions, components, parts, or combinations thereof, may exist or may be added.

Further, components that will be described in the specification are discriminated merely according to functions mainly performed by the components. That is, two or more components which will be described later can be integrated into a single component. Furthermore, a single component can be separated into two or more components. Moreover, each component can additionally perform some or all of a function executed by another component in addition to the main function thereof. Some or all of the main function of each component can be carried out by another component. Each component may be implemented as hardware, software, or a combination of both.

FIG. 1 is a block diagram illustrating an apparatus for measuring bio-information according to an embodiment.

Referring to FIG. 1, the apparatus 10 for measuring bio-information includes a touch pen 100 and an electronic device 200.

The touch pen 100 is a device for inputting data into the electronic device 200 by touching a touch screen of the electronic device 200, and may be referred to as an electronic pen, a stylus, a stylus pen, a smart pen, and the like.

In response to a touch of a user's finger while the touch pen 100 is placed on the touch screen of the electronic device 200, the touch pen 100 may measure a pulse wave signal of the user through the finger touching the touch pen 100, and may transmit the measured pulse wave signal to the electronic device 200. Here, the pulse wave signal may be a Photoplethysmogram (PPG) signal.

The electronic device 200 is a device that performs various functions by receiving touch-based inputs. Examples of the electronic device 200 may include a cellular phone, a smartphone, a tablet personal computer (PC), a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

The electronic device 200 may receive the user's pulse wave signal from the touch pen 100, and may estimate bio-information of the user based on the received pulse wave signal. Here, bio-information may include blood pressure, blood glucose, cholesterol, vascular age, arterial stiffness, aortic pressure waveform, vascular compliance, stress index, fatigue level, and the like, but is not limited thereto. For convenience of explanation, the following description will be given using blood pressure as an example of bio-information.

In an embodiment, the touch pen 100 and the electronic device 200 may be formed as at least one of an electromagnetic induction type device, an active electrostatic type device, a resistive type device, and a capacitive type device.

Figure 2:
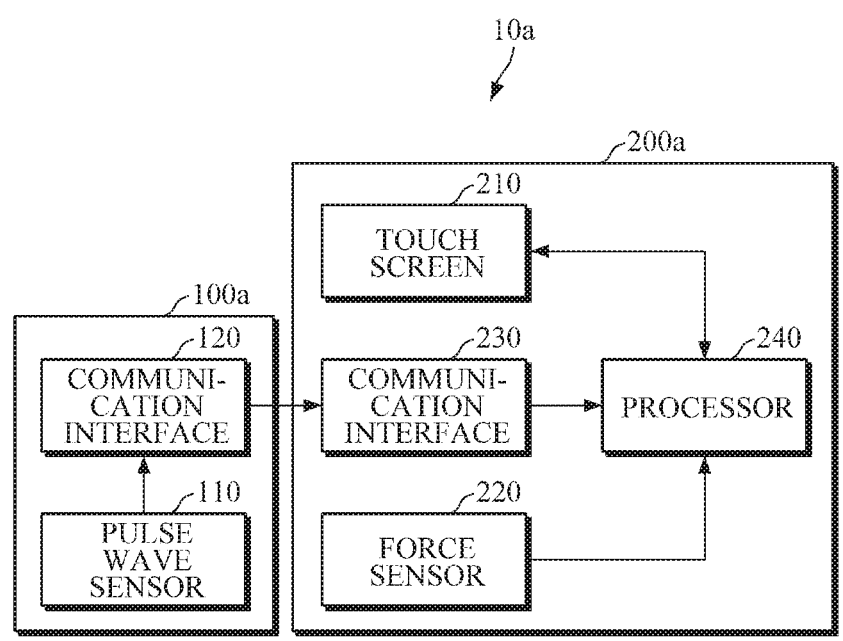
FIG. 2 is a detailed block diagram of an apparatus for measuring bio-information according to an embodiment.
Figure 3:
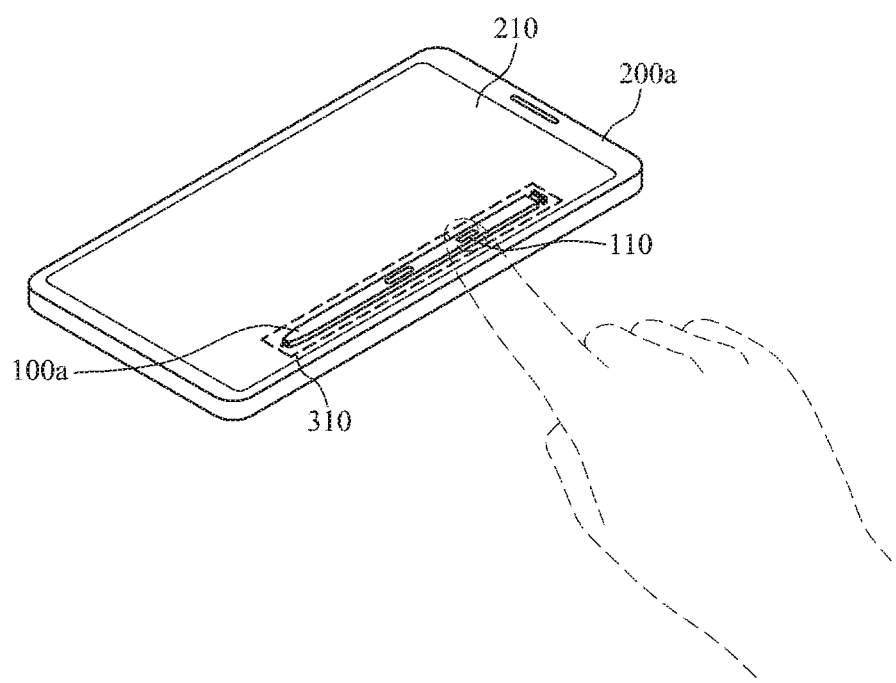
FIG. 3 is a diagram illustrating an example of a position guideline of a touch pen according to an embodiment.
Figure 4:
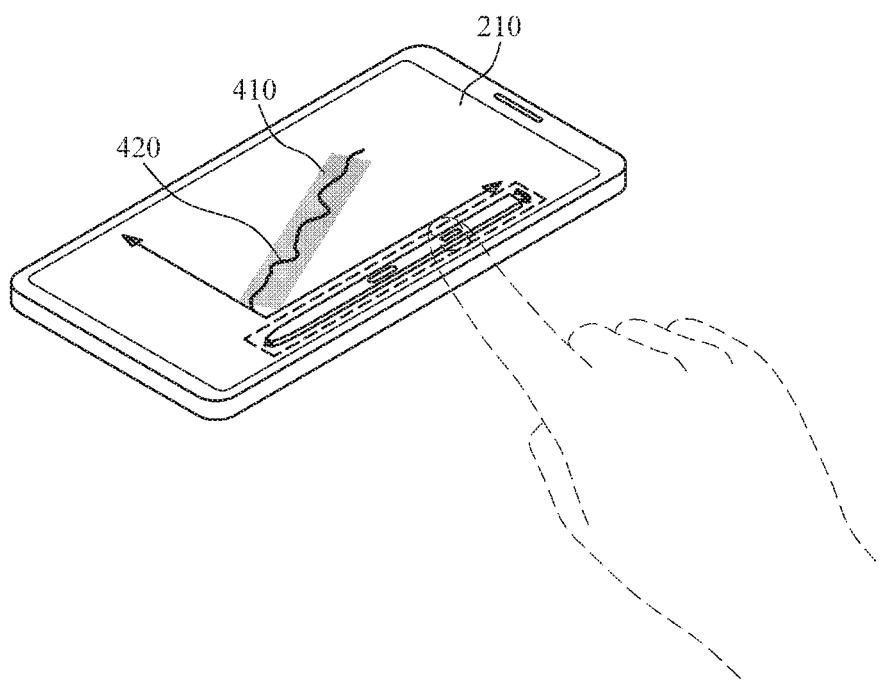
FIG. 4 is a diagram illustrating an example of a force guide information according to an embodiment.
Figure 5:
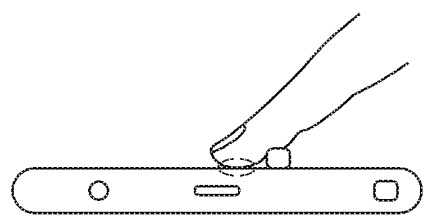
FIG. 5 is a diagram illustrating an example of an inappropriate measurement posture.
Figure 6:
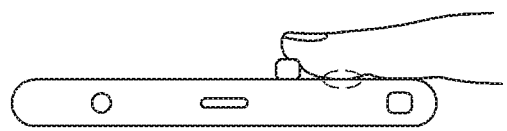
FIG. 6 a diagram illustrating another example of an inappropriate measurement posture.

FIG. 2 is a detailed block diagram of an apparatus for measuring bio-information according to an embodiment of the present disclosure; FIG. 3 is a diagram illustrating an example of a position guideline of a touch pen; FIG. 4 is a diagram illustrating an example of a force guide information; and FIGS. 5 and 6 are diagrams illustrating examples of an inappropriate measurement posture. The apparatus 10a for measuring bio-information of FIG. 2 may be an example of the apparatus 10 for measuring bio-information of FIG. 1.

Referring to FIG. 2, the apparatus 10a for measuring bio-information includes a touch pen 100a and an electronic device 200a.

The touch pen 100a includes a pulse wave sensor 110 and a communication interface 120.

When a user's finger touches the pulse wave sensor 110 while the touch pen 100a is placed on a touch screen 210 of the electronic device 200a, the pulse wave sensor 110 may measure one or more pulse wave signals through the finger touching the pulse wave sensor 110. In the case where the pulse wave sensor 110 measures a plurality of pulse wave signals, the plurality of pulse wave signals may be pulse wave signals measured by using light of different wavelengths. In an embodiment, the pulse wave sensor 110 includes one or more light sources for emitting light to the user's finger touching the pulse wave sensor 110, and one or more photodetectors for receiving light returning from the finger.

In an embodiment, the pulse wave sensor 110 may be formed to have a contact surface, which is curved convexly toward a user's finger being in contact with the contact surface.

The communication interface 120 may communicate with the electronic device 200a. For example, the communication interface 120 may transmit the measured pulse wave signal to the electronic device 200a. In an embodiment, the communication interface 120 may communicate with the electronic device 200a by using various communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G) communication, fourth generation (4G) communication, fifth generation (5G) communication, and the like.

The electronic device 220a includes a touch screen 210, a force sensor 220, a communication interface 230, and a processor 240.

The touch screen 210 may detect touch of the touch pen 100a or a user's skin, and may receive a touch-based input. Further, the touch screen 210 may visually output data used by the electronic device 220a and/or processing result data of the electronic device 220a under the control of the processor 240.

While the pulse wave sensor 110 of the touch pen 100a measures a pulse wave signal, the force sensor 220 may measure a pressing force of the finger pressing the pulse wave sensor 110. In an embodiment, the force sensor 220 may be disposed at a lower portion of the touch screen 210. The force sensor 220 may include a voltage-resistance force sensor, an ultrasonic force sensor, a load cell sensor, a capacitive force sensor, a pyroelectric force sensor, a strain-gauge force sensor, an electrochemical force sensor, an optical force sensor, a magnetic force sensor, and the like.

The communication interface 230 may communicate with the touch pen 100a. For example, the communication interface 230 may receive the pulse wave signal from the touch pen 100a. In an embodiment, the communication interface 230 may communicate with the touch pen 100a by using various communication techniques such as Bluetooth communication, BLE communication, NFC, WLAN communication, Zigbee communication, IrDA, WFD communication, UWB communication, Ant+ communication, Wi-Fi communication, RFID communication, 3G communication, 4G communication, 5G communication, and the like.

The processor 240 may control the overall operation of the electronic device 200a.

When a specific event occurs, such as an instruction for measuring blood pressure and the like, the processor 240 may display a guideline (hereinafter referred to as a "touch pen position guideline"), indicating a position to place the touch pen 100a for measuring blood pressure, in a portion of the touch screen 210. For example, as illustrated in FIG. 3, the processor 240 may display a touch pen position guideline 310 in a portion of the touch screen 210 of the electronic device 200a.

The touch pen position guideline 310 may provide a user with information on whether a direction of a finger pressing the pulse wave sensor 110 is correct. In order to measure blood pressure, a user may place the touch pen 100a on the touch pen position guideline 310, displayed on the touch screen 210 of the electronic device 200a, with the pulse wave sensor 110 facing upward, and may press the pulse wave sensor 110 of the touch pen 100a with a finger vertically from above. In this case, if the user presses the pulse wave sensor 110 with the finger in a direction other than the vertical direction, the touch pen 100a may be moved in a direction of force exerted on the pulse wave sensor 110, and as a result, the touch pen 100a may deviate from the touch pen position guideline 310. Accordingly, by observing whether the touch pen 100a deviates from the touch pen position guideline 310, the user may check whether the user's finger presses the pulse wave sensor 110 in an appropriate direction. In this manner, the user may reduce quality degradation which occurs depending on a pressing direction.

The processor 240 may generate action guide information for guiding a user's action to measure a user's pulse wave signal by using the touch pen 100a, and may output the generated action guide information through an output device. In this case, the output device may be the touch screen 210, but is not limited thereto, and may include an audio output device (e.g., speaker, etc.), a tactile output device (e.g., vibrator, etc.), and the like. The action guide information may include information for guiding a user to place the touch pen 100 on the touch screen (e.g., information for guiding a user to place the touch pen 100 on the touch pen position guideline 310 and to touch the pulse wave sensor 110 of the touch pen 100 with a finger), and the like.

Based on the force value measured by the force sensor 220, the processor 240 may generate force guide information for guiding a force to be increased or decreased by a user for the pulse wave sensor 110 while the touch pen 100a measures a pulse wave signal, and may provide the force guide information for the user through an output device. In this case, the output device may be the touch screen 210, but is not limited thereto, and may include an audio output device (e.g., speaker, etc.), a tactile output device (e.g., vibrator, etc.), and the like. The force guide information may be provided before, after, or concurrently with a time when the pulse wave sensor 110 of the touch pen 100a starts to measure a pulse wave signal, and may be provided continuously while the pulse wave sensor 110 of the touch pen 100a measures the pulse wave signal. The force guide information may be predetermined for each user based on user characteristics such as a user's age, sex, health condition, and the like. In an embodiment, as illustrated in FIG. 4, the force guide information may include a force guideline 410, indicating a range of a desired force, and a force value 420 measured by the force sensor 220. However, the force guide information is not limited thereto, and may be a force value itself to be increased or decreased by a user for the pulse wave sensor 110. Further, the force guide information may include a user's action information and the like for inducing a change in pressing force of a finger pressing the pulse wave sensor 110.

While the pulse wave sensor 110 measures the pulse wave signal, the processor 240 may determine whether a user's measurement posture is appropriate. For example, as illustrated in FIGS. 5 and 6, during measurement of the pulse wave signal, when the user's finger touches the touch screen 210 at a position near an area where the touch pen 100a is placed, the processor 240 may determine that the user's measurement posture is inappropriate. Further, based on determining that the user's measurement posture is inappropriate, the processor 240 may generate a warning signal, and may warn a user through an output device. In this manner, the electronic device 200a may reduce quality deterioration in measured bio-information, which occurs due to an inappropriate measurement posture.

The processor 240 may estimate a user's blood pressure based on the pulse wave signal received from the touch pen 100a and the force value measured by the force sensor 220. For example, the processor 240 may calculate contact pressure between the pulse wave sensor 110 of the touch pen 100a and the finger based on the force value measured by the force sensor 220 and a predetermined area value, and may estimate a user's blood pressure by analyzing a change in the pulse wave signal according to a change in the contact pressure.

Blood pressure may include Diastolic Blood Pressure (DBP), Systolic Blood Pressure (SBP), and Mean Arterial Pressure (MAP); and the contact pressure applied to the finger may act as an external pressure on the blood vessels. If the contact pressure is lower than the MAP, an elastic restoring force of tissues act to constrict the blood vessels, such that the amplitude of the pulse wave signal is reduced; if the contact pressure is equal to the MAP, the elastic restoring force of tissues becomes zero, having no effect on the blood vessels, such that the amplitude of the pulse wave signal reaches its peak value. Further, if the contact pressure is greater than the MAP, the elastic restoring force of tissues act to dilate the blood vessels, such that the amplitude of the pulse wave signal is reduced. Accordingly, by analyzing the change in pulse wave signal according to the change in contact pressure, the processor 240 may estimate, as the MAP, a contact pressure value at a point where an amplitude value of the pulse wave signal is maximum. Further, the processor 240 may estimate, as the systolic blood pressure (SBP), a contact pressure value at a point where an amplitude value has a first ratio (e.g., 0.6) to the maximum amplitude value of the pulse wave signal; and may estimate, as the diastolic blood pressure (DBP), a contact pressure value at a point where an amplitude value has a second ratio (e.g., 0.7) to the maximum amplitude value of the pulse wave signal. In this case, correlations may be pre-defined by experiments, including a correlation between a contact pressure value, at a point where an amplitude of the pulse wave signal is maximum, and MAP; a correlation between a contact pressure value, at a point where an amplitude value has the first ratio to the maximum amplitude value, and SBP; and a correlation between a contact pressure value, at a point where an amplitude value has the second ratio to the maximum amplitude, and DBP.

In another example, the processor 240 may estimate a user's blood pressure by analyzing a change in the pulse wave signal according to a change in the force value measured by the force sensor 220. That is, without calculating contact pressure between the pulse wave sensor 110 of the touch pen 100a and the finger, the processor 240 may estimate a user's blood pressure by analyzing the change in the pulse wave signal according to the change in the measured force value. For example, based on analyzing the change in the pulse wave signal according to the change in the force value, the processor 240 may estimate MAP by using a force value at a point where an amplitude of the pulse wave signal is maximum, may estimate SBP by using a force value at a point where an amplitude value has the first ratio (e.g., 0.6) to the maximum amplitude value of the pulse wave signal, and may estimate DBP by using a force value at a point where an amplitude value has the second ratio (e.g., 0.7) to the maximum amplitude value of the pulse wave signal. In this case, correlations may be pre-defined by experiments, including a correlation between a force value, at a point where an amplitude of the pulse wave signal is maximum, and MAP; a correlation between a force value, at a point where an amplitude value has the first ratio to the maximum amplitude value of the pulse wave signal, and SBP; and a correlation between a force value, at a point where an amplitude value has the second ratio to the maximum amplitude value of the pulse wave signal, and DBP.

FIGS. 7 to 10 are block diagrams illustrating examples of a pulse wave sensor. FIGS. 7 to 10 may be examples of the pulse wave sensor 110 of FIG. 2.

Figure 7:
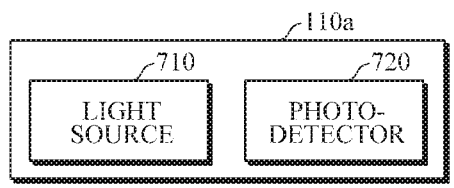
FIG. 7 is a block diagram illustrating an example of a pulse wave sensor according to an embodiment.

Referring to FIG. 7, the pulse wave sensor 110a according to an embodiment of the present disclosure includes a light source 710 and a photodetector 720.

The light source 710 may emit light of a predetermined wavelength onto a user's finger. In an embodiment, the light source 710 may emit visible light, Near Infrared (NIR) light, and Mid Infrared (MIR) light. However, wavelengths of light emitted by the light source 710 may vary depending on the types of bio-information desired to be measured. Further, the light source 710 might not necessarily be formed of a single light-emitting body, and may be formed of an array of a plurality of light-emitting bodies. In an embodiment, the light source 710 may include a light emitting diode (LED), a laser diode, a phosphor, and the like.

The photodetector 720 may measure a user's pulse wave signal by detecting light reflected or scattered from the user's finger. In an embodiment, the photodetector 720 may include a photo diode, a photo transistor (PTr), an image sensor (e.g., a charge-coupled device (CCD), a Complementary Metal-Oxide Semiconductor (CMOS), etc.), and the like, but is not limited thereto.

Figure 8:
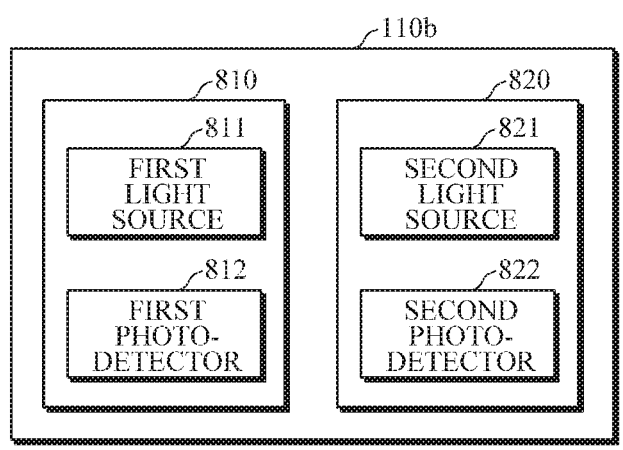
FIG. 8 is a block diagram illustrating another example of a pulse wave sensor according to an embodiment.

Referring to FIG. 8, a pulse wave sensor 110b according to another embodiment of the present disclosure may be formed of an array of pulse wave measurers for measuring a plurality of pulse wave signals. As illustrated in FIG. 8, the pulse wave sensor 110b includes a first pulse wave measurer 810 and a second pulse wave measurer 820. While FIG. 8 illustrates two pulse wave measurers, this is merely for convenience of explanation, and the number of pulse wave measurers included in the pulse wave sensor 110b is not specifically limited.

The first pulse wave measurer 810 includes a first light source 811 for emitting light of a first wavelength onto an object, and a first photodetector 812 for measuring a first pulse wave signal by receiving the light of the first wavelength which is emitted by the first light source 811 and returns from the object.

The second pulse wave measurer 820 includes a second light source 821 for emitting light of a second wavelength onto the object, and a second photodetector 822 for measuring a second pulse wave signal by receiving the light of the second wavelength which is emitted by the second light source 821 and returns from the object. Here, the first wavelength and the second wavelength may be different from each other.

Figure 9:
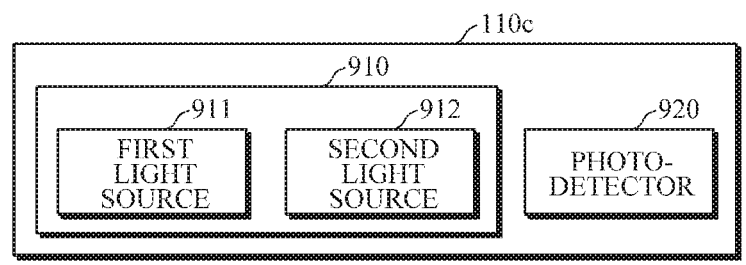
FIG. 9 is a block diagram illustrating yet another example of a pulse wave sensor according to an embodiment.

Referring to FIG. 9, a pulse wave sensor 110c according to yet another embodiment of the present disclosure includes a light source part 910, including a plurality of light sources 911 and 912, and a photodetector 920. While FIG. 9 illustrates two light sources, this is merely for convenience of explanation, and the number of light sources included in the light source part 910 is not specifically limited.

The first light source 911 may emit light of a first wavelength onto a user's finger, and the second source 912 may emit light of a second wavelength onto the finger. In this case, the first wavelength and the second wavelength may be different from each other.

The first light source 911 and the second light source 912 may be driven in a time-division manner according to a predetermined control signal to sequentially or simultaneously emit light onto the user's finger. In this case, light source driving conditions, including an emission time, a driving sequence, a current intensity, a pulse duration, and the like, of the light sources 911 and 912, may be preset. The pulse wave sensor 110c may drive each of the light sources 911 and 912 by referring to the light source driving conditions.

The photodetector 920 may measure a first pulse wave signal and a second pulse wave signal by simultaneously or sequentially detecting the light of the first wavelength and the light of the second wavelength which are simultaneously or sequentially emitted by the first light source 911 and the second light source 912 onto the object and return from the object.

Figure 10:
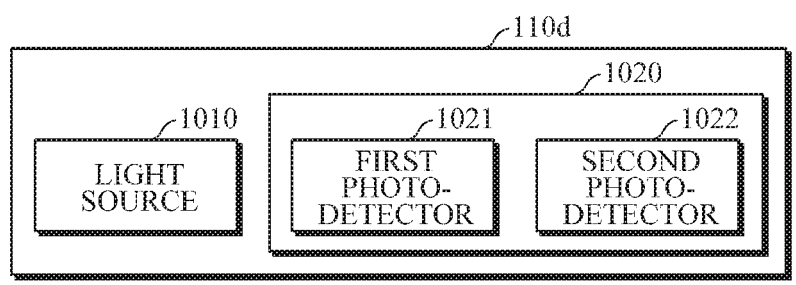
FIG. 10 is a block diagram illustrating still example of a pulse wave sensor according to an embodiment.

Referring to FIG. 10, a pulse wave sensor 110d according to still another embodiment of the present disclosure includes a light source 1010 and a photodetector part 1020. The photodetector part 1020 includes a first photodetector 1021 and a second photodetector 1022. While FIG. 10 illustrates two photodetectors, this is merely for convenience of explanation, and the number of photodetectors included in the photodetector part 1020 is not specifically limited.

The light source 1010 may emit light of a predetermined wavelength onto a user's finger. In this case, the light source 1010 may emit light in a wide wavelength range including a visible light.

The photodetector part 1020 may measure a plurality of pulse wave signals by receiving light in a predetermined wavelength range which returns from the user's finger. To this end, the photodetector part 1020 may have a plurality of different response characteristics.

For example, the first photodetector 1021 and the second photodetector 1022 may be formed as photo diodes having different measurement ranges so as to respond to light of different wavelengths which return from the user's finger. Alternatively, in order to allow the first photodetector 1021 and the second photodetector 1022 to respond to light of different wavelengths, a filter may be provided on a front surface of any one of the first photodetector 1021 and the second photodetector 1022, or different filters may be provided on front surfaces of the two photodetectors 1021 and 1022. Further, the first photodetector 1021 and the second photodetector 1022 may be disposed at different distances from the light source 1010. In this case, a photodetector disposed at a relatively short distance from the light source 1010 may detect light in a short wavelength range, and a photodetector disposed at a relatively long distance from the light source 1010 may detect light in a long wavelength range.

Embodiments of the pulse wave sensor for measuring one or more pulse wave signals are described above with reference to FIGS. 7 to 10. However, these are merely examples, and the pulse wave sensor is not limited thereto. There may be various numbers and arrangements of light sources and photodetectors, and the number and arrangement thereof may vary according to the purpose of use of the pulse wave sensor, the size and shape of a touch pen in which the pulse wave sensor is mounted, and the like.

Figure 11:
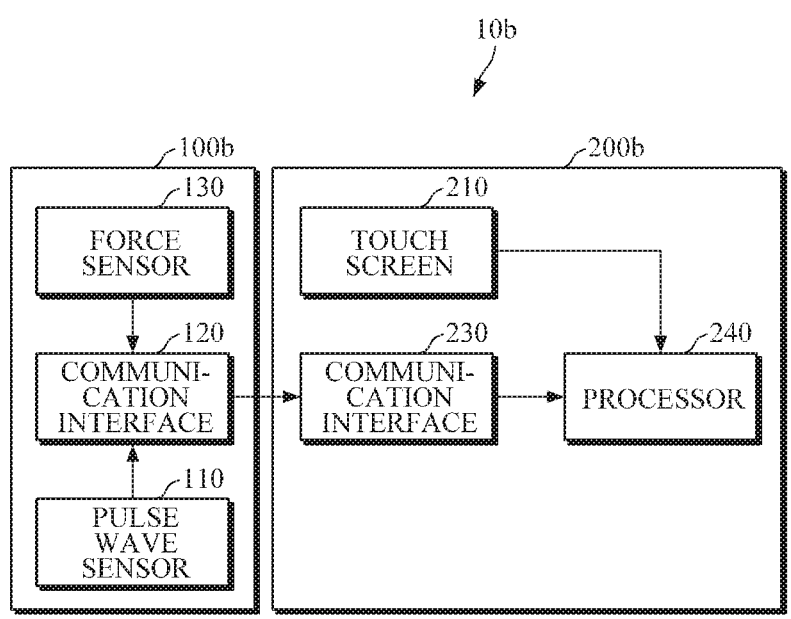
FIG. 11 is a detailed block diagram illustrating an apparatus for measuring bio-information according to another embodiment.

FIG. 11 is a detailed block diagram illustrating an apparatus for measuring bio-information according to another embodiment of the present disclosure. The apparatus 10b for measuring bio-information of FIG. 11 may be another example of the apparatus 10 for measuring bio-information of FIG. 1.

Referring to FIG. 11, the apparatus 10b for measuring bio-information includes a touch pen 100b and an electronic device 200b. The touch pen 100b includes a pulse wave sensor 110, a communication interface 120, and a force sensor 130, and the electronic device 200b includes a touch screen 210, a communication interface 230, and a processor 240. That is, unlike the apparatus 10a for measuring bio-information of FIG. 2, the apparatus 10b for measuring bio-information may include the force sensor 130 which is mounted in the touch pen 100b.

The force sensor 130 may be mounted in the touch pen 100b, and while the pulse wave sensor 110 measures a pulse wave signal, the force sensor 130 may measure a pressing force of a finger pressing the pulse wave sensor 110. In an embodiment, the force sensor 130 may be disposed at a lower portion of the pulse wave sensor 110.

The communication interface 120 of the touch pen 100b may transmit the force value, measured by the force sensor 130, to the electronic device 200b, and the communication interface 230 of the electronic device 200b may receive the force value from the touch pen 100b. The processor 240 of the electronic device 200b may generate force guide information based on the received force value, and may provide the generated force guide information for a user through an output device.

The pulse wave sensor 110 of the touch pen 100b, and the touch screen 210 and the processor 240 of the electronic device 200b are described above with reference to FIGS. 2 to 10, such that detailed description thereof will be omitted.

Figure 12:
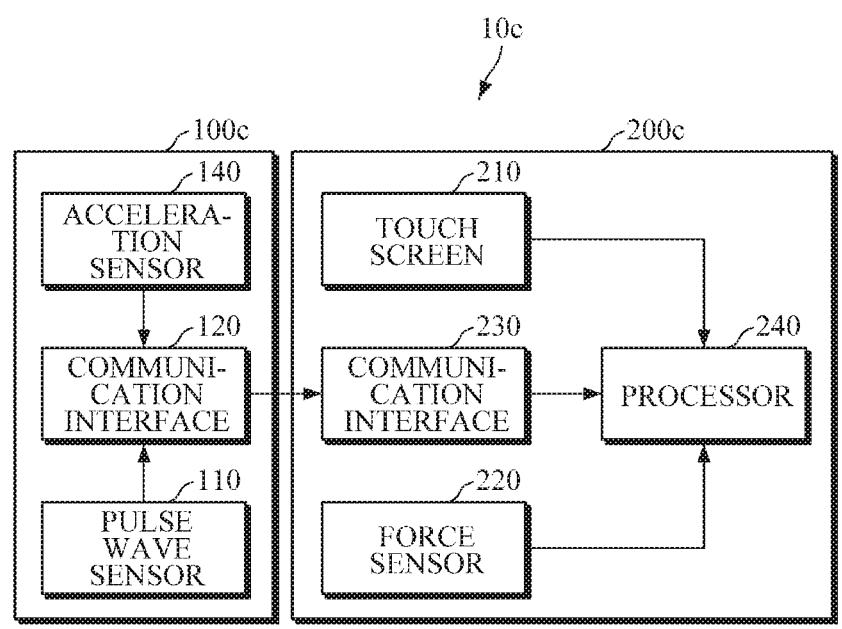
FIG. 12 is a detailed block diagram illustrating an apparatus for measuring bio-information according to yet another embodiment.

FIG. 12 is a detailed block diagram illustrating an apparatus for measuring bio-information according to yet another embodiment of the present disclosure. The apparatus 10c for measuring bio-information of FIG. 12 may be yet another example of the apparatus 10 for measuring bio-information of FIG. 1.

Referring to FIG. 12, the apparatus 10c for measuring bio-information includes a touch pen 100c and an electronic device 200c. The touch pen 100c includes a pulse wave sensor 110, a communication interface 120, and an acceleration sensor 140, and the electronic device 200c includes a touch screen 210, a force sensor 220, a communication interface 230, and a processor 240. That is, unlike the apparatus 10a for measuring bio-information of FIG. 2, the apparatus 10c for measuring bio-information may include the touch pen 100c which further includes the acceleration sensor 140.

The acceleration sensor 140 may measure acceleration of the touch pen 100c, and may determine whether the touch pen 100c is moved based on the measured acceleration value. If the touch pen 100c is moved, the acceleration sensor 140 may generate a warning signal, and may warn a user through an output device. In order to measure blood pressure, a user may place the touch pen 100a in a portion of the touch screen 210 of the electronic device 200a with the pulse wave sensor 110 facing upward, and may press the pulse wave sensor 110 of the touch pen 100a with a finger vertically from above. In this case, if the user presses the pulse wave sensor 110 with a finger in a direction other than the vertical direction, the touch pen 100a may be moved in a direction of force exerted on the pulse wave sensor 110. Accordingly, by determining whether the touch pen 100c is moved, information on whether the user presses the pulse wave sensor 110 in an appropriate direction may be provided. In this manner, the apparatus 10c for measuring bio-information may reduce quality degradation which occurs depending on the user's pressing direction.

Further, in an embodiment, the acceleration sensor 140 may simply measure only acceleration of the touch pen 100c, and the electronic device 200c may determine whether the touch pen 100c is moved and may generate a warning signal. In this case, the communication interface 120 of the touch pen 100c may transmit the acceleration value, measured by the acceleration sensor 140, to the electronic device 200c, and the communication interface 230 of the electronic device 200c may receive the acceleration value from the touch pen 100c. The processor 240 of the electronic device 200c may determine whether the touch pen 100c is moved based on the received acceleration value, and based on determining that the touch pen 100c is moved, the processor 240 may generate a warning signal and may warn a user through an output device.

In addition, the pulse wave sensor 110 and the communication interface 120 of the touch pen 100c, and the touch screen 210, the force sensor 220, the communication interface 230, and the processor 240 of the electronic device 200b are described above with reference to FIGS. 2 to 10, such that detailed description thereof will be omitted.

Figure 13:
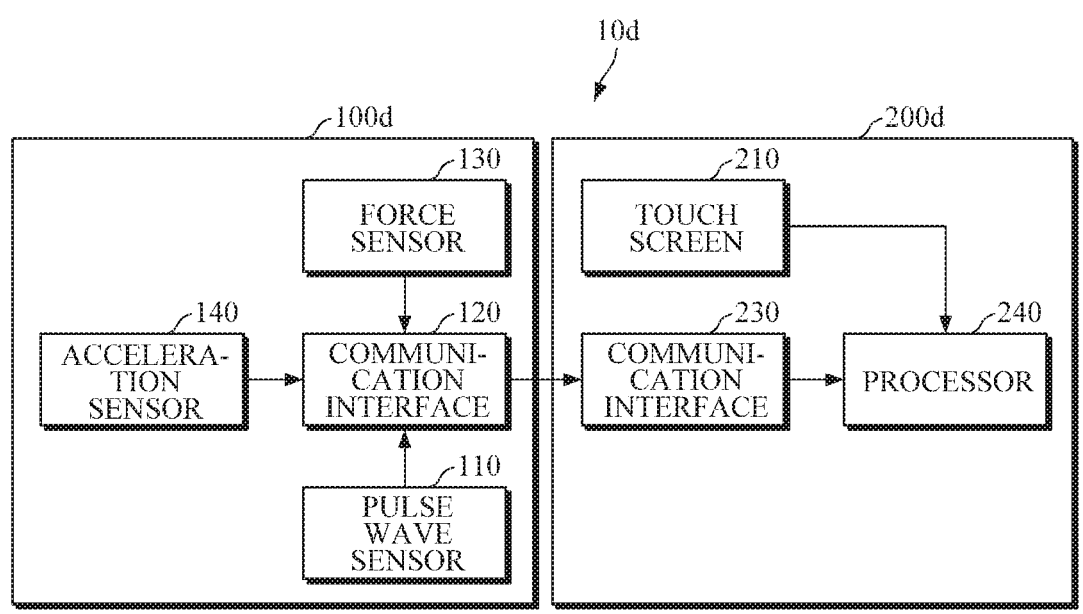
FIG. 13 is a detailed block diagram illustrating an apparatus for measuring bio-information according to still another embodiment.

FIG. 13 is a detailed block diagram illustrating an apparatus for measuring bio-information according to still another embodiment of the present disclosure. The apparatus 10d for measuring bio-information of FIG. 13 may be still another example of the apparatus 10 for measuring bio-information of FIG. 1.

Referring to FIG. 13, the apparatus 10d for measuring bio-information includes a touch pen 100d and an electronic device 200d. The touch pen 100d includes a pulse wave sensor 110, a communication interface 120, a force sensor 130, and an acceleration sensor 140, and the electronic device 200c includes a touch screen 210, a communication interface 230, and a processor 240. That is, unlike the apparatus 10a for measuring bio-information of FIG. 2, the apparatus 10d for measuring bio-information includes the force sensor which may be mounted in the touch pen 100d, and the touch pen 100d may further include the acceleration sensor 140.

The pulse wave sensor 110, the communication interface 120, the force sensor 130, and the acceleration sensor 140 of the touch pen 100d, and the touch screen 210, the communication interface 230, and the processor 240 of the electronic device 200b are described above with reference to FIGS. 2 to 12, such that detailed description thereof will be omitted.

Figure 14:
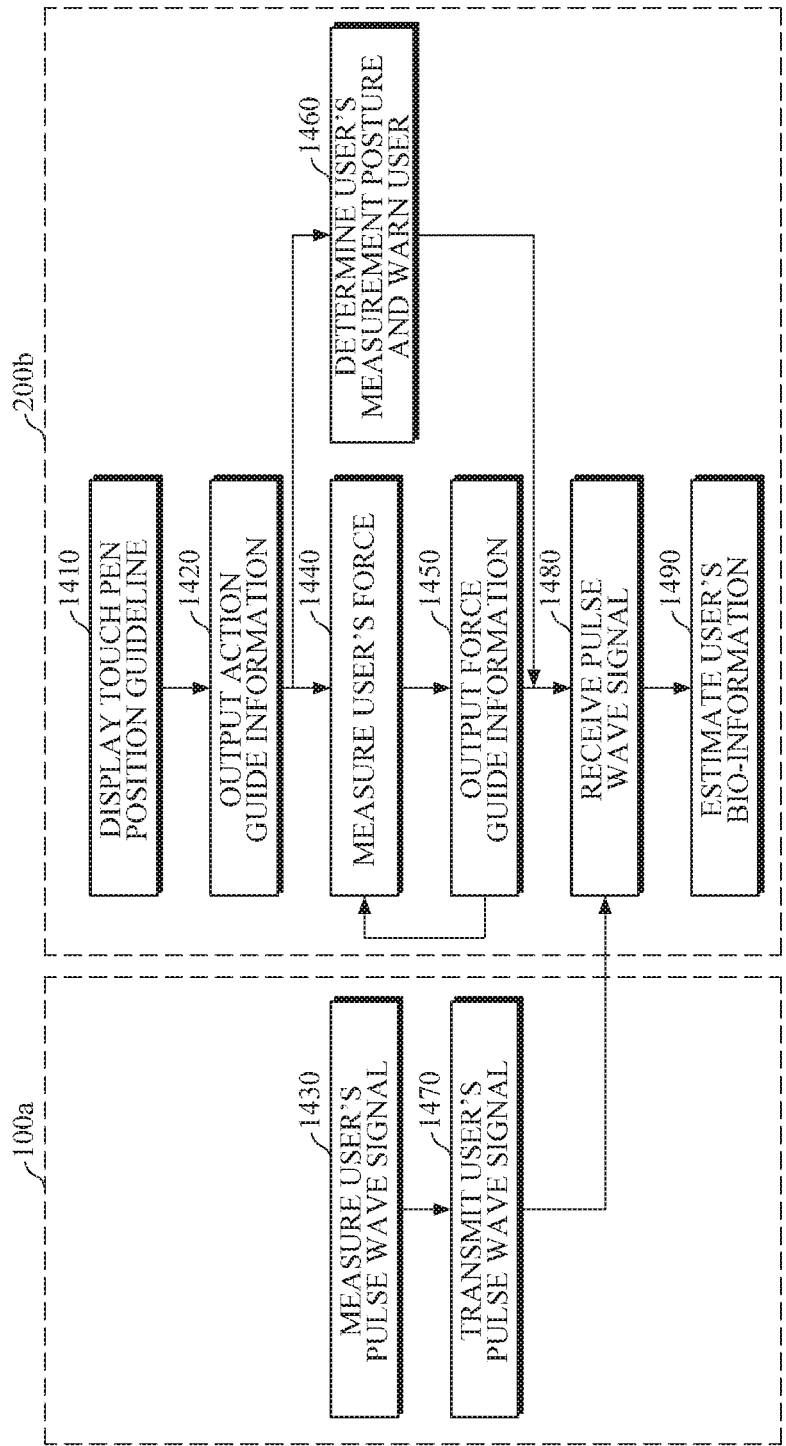
FIG. 14 is a flowchart illustrating a method of measuring bio-information according to an embodiment.

FIG. 14 is a flowchart illustrating a method of measuring bio-information according to an embodiment of the present disclosure. The method of measuring bio-information of FIG. 14 may be performed by the apparatus 10a for measuring bio-information of FIG. 2.

Referring to FIG. 14, when a specific event occurs, such as an instruction for measuring blood pressure and the like, the electronic device 200a may display a touch pen position guideline, indicating a position to place the touch pen 100a for measuring blood pressure, in a portion of the touch screen in operation 1410.

The electronic device 200a may generate action guide information for guiding a user's action to measure a pulse wave signal by using the touch pen 100a, and may output the generated action guide information through an output device in operation 1420.

When a user's finger touches the pulse wave sensor after placing the touch pen 100a on the touch pen position guideline according to the action guide information, the touch pen 100a may measure one or more pulse wave signals through the finger touching the pulse wave sensor in operation 1430.

While the touch pen 100a measures the pulse wave signals, the electronic device 200a may measure a pressing force of the finger pressing the pulse wave sensor of the touch pen 100a in operation 1440.

Based on the measured force value, the electronic device 200a may generate force guide information for guiding a force to be increased or decreased by the user for the pulse wave sensor of the touch pen 100a while touch pen 100a measures the pulse wave signals, and may provide the force guide information for the user through an output device in operation 1450. In this case, the electronic device 200a may provide the force guide information before, after, or concurrently with, a time when the pulse wave sensor of the touch pen 100a starts to measure the pulse wave signals, and may provide the force guide information continuously while the pulse wave sensor of the touch pen 100a measures the pulse wave signals.

While the touch pen 100a measures the pulse wave signals, the electronic device 200a may determine whether a user's measurement posture is appropriate, and based on determining that user's measurement posture is inappropriate, the electronic device 200a may generate a warning signal and may warn the user through an output device in operation 1460. For example, while the touch pen 100a measures the pulse wave signals, when the user's finger touches the touch screen of the electronic device 200a at a position near an area where the touch pen 100a is placed, the electronic device 200a may determine that the user's measurement posture is inappropriate.

The touch pen 100a may transmit the measured pulse wave signals to the electronic device 200a in operation 1470, and the electronic device 200b may receive the pulse wave signals from the touch pen 100a in operation 1480. In this case, the touch pen 100a and the electronic device 200a may communicate with each other using various communication techniques described above.

The electronic device 200a may estimate a user's bio-information based on the pulse wave signals, received from the touch pen 100a, and the measured force value in operation 1490. For example, the electronic device 200a may calculate contact pressure between the pulse wave sensor of the touch pen 100a and the finger based on the measured force value and a predetermined area value, and may estimate a user's blood pressure by analyzing a change in the pulse wave signal according to a change in the contact pressure. In another example, without calculating contact pressure between the pulse wave sensor 110 of the touch pen 100a and the finger, the electronic device 200a may estimate the user's blood pressure by analyzing the change in the pulse wave signal according to a change in the measured force value.

Figure 15:
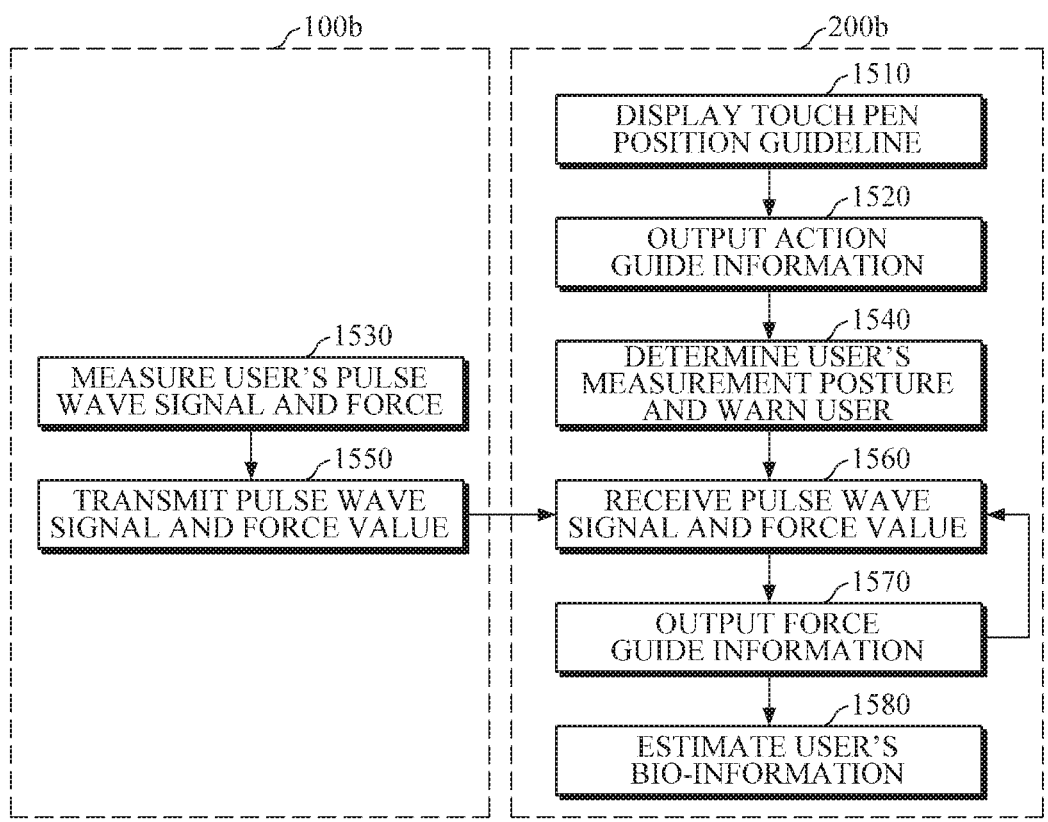
FIG. 15 is a flowchart illustrating a method of measuring bio-information according to another embodiment.

FIG. 15 is a flowchart illustrating a method of measuring bio-information according to another embodiment of the present disclosure. The method of measuring bio-information of FIG. 15 may be performed by the apparatus 10b for measuring bio-information of FIG. 11.

Referring to FIG. 15, when a specific event occurs, such as an instruction for measuring blood pressure and the like, the electronic device 200b may display a touch pen position guideline, indicating a position to place the touch pen 100b for measuring blood pressure, in a portion of the touch screen in operation 1510.

The electronic device 200b may generate action guide information for guiding a user's action to measure a pulse wave signal by using the touch pen 100b, and may output the generated action guide information through an output device in operation 1520.

When a user's linger touches the pulse wave sensor after placing the touch pen 100b on the touch pen position guideline according to the action guide information, the touch pen 100b may measure one or more pulse wave signals and a pressing force of the finger pressing the touch pen 100b in operation 1530.

While the touch pen 100b measures the pulse wave signals, the electronic device 200b may determine whether a user's measurement posture is appropriate, and based on determining that user's measurement posture is inappropriate, the electronic device 200b may generate a warning signal and may warn the user through an output device in operation 1540.

The touch pen 100b may transmit the measured pulse wave signals and force value to the electronic device 200b in operation 1550, and the electronic device 200b may receive the pulse wave signals and the force value from the touch pen 100b in operation 1560. In this case, the touch pen 100b and the electronic device 00b may communicate with each other using various communication techniques described above.

Based on the received force value, the electronic device 200b may generate force guide information for guiding a force to be increased or decreased by the user for the pulse wave sensor of the touch pen 100b while the touch pen 100b measures the pulse wave signals, and may provide the force guide information for the user through an output device in operation 1570.

The electronic device 200b may estimate the user's bio-information based on the pulse wave signals, received from the touch pen 100b, and the force value in operation 1580.

Figure 16:
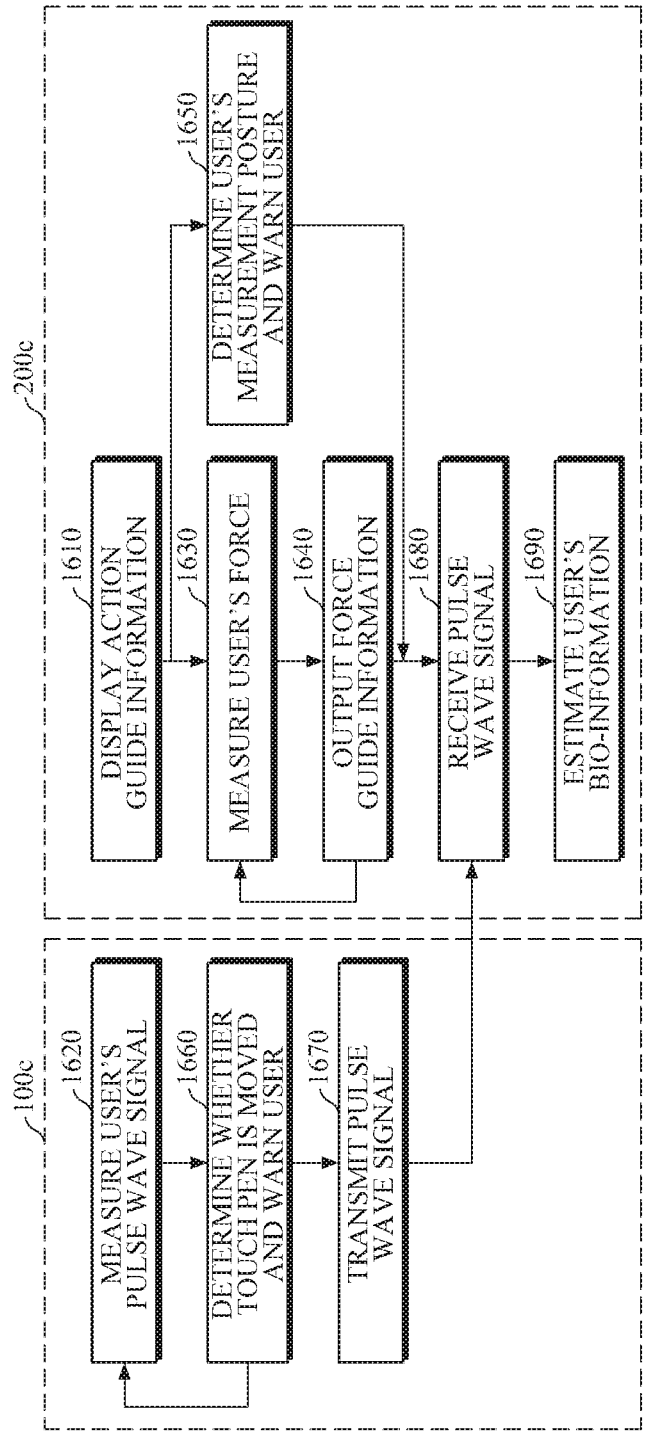
FIG. 16 is a flowchart illustrating a method of measuring bio-information according to yet another embodiment.

FIG. 16 is a flowchart illustrating a method of measuring bio-information according to yet another embodiment of the present disclosure. The method of measuring bio-information of FIG. 16 may be performed by the apparatus 10c for measuring bio-information of FIG. 12.

Referring to FIG. 16, when a specific event occurs, such as an instruction for measuring blood pressure and the like, the electronic device 200c may generate action guide information for guiding a user's action to measure a user's pulse wave signal by using the touch pen 100c, and may output the generated action guide information through an output device in operation 1610.

When a user places the touch pen 100c on a touch screen of the electronic device 200c according to the action guide information and touches the pulse wave sensor with a finger, the touch pen 100c may measure one or more pulse wave signals through the finger touching the pulse wave sensor in operation 1620.

While the touch pen 100c measures the pulse wave signals, the electronic device 200c may measure a pressing force of the finger pressing the pulse wave sensor of the touch pen 100c in operation 1630.

Based on the received force value, the electronic device 200c may generate force guide information for guiding a force to be increased or decreased by the user for the pulse wave sensor of the touch pen 100c while the touch pen 100c measures the pulse wave signal, and may provide the force guide information for the user through an output device in operation 1640.

While the touch pen 100c measures the pulse wave signals, the electronic device 200c may determine whether a user's measurement posture is appropriate, and based on determining that user's measurement posture is inappropriate, the electronic device 200c may generate a warning signal and may warn the user through an output device in operation 1650.

While the touch pen 100c measures the pulse wave signals, the electronic device 200c may measure acceleration of the touch pen 100c, and determine whether the touch pen 100c is moved based on the measured acceleration value. Based on determining that the touch pen 100c is moved, the electronic device 200c may generate a warning signal and may warn the user through an output device in operation 1660.

The touch pen 100c may transmit the measured pulse wave signals to the electronic device 200c in operation 1670, and the electronic device 200c may receive the pulse wave signals from the touch pen 100c in operation 1680. In this case, the touch pen 100c and the electronic device 200c may communicate with each other using various communication techniques described above.

The electronic device 200c may estimate the user's bio-information based on the pulse wave signals, received from the touch pen 100c, and the force value in operation 1690.

Further, in an embodiment, regarding operation 1660, the touch pen 100c may simply measure only acceleration of the touch pen 100c, and the electronic device 200c may determine whether the touch pen 100c is moved and may generate a warning signal. In this case, the touch pen 100c may transmit the measured acceleration value to the electronic device 200c, and the electronic device 200c may receive the acceleration value from the touch pen 100c. Further, the electronic device 200c may determine whether the touch pen 100c is moved based on the received acceleration value, and based on determining that the touch pen 100c is moved, the electronic device 200c may generate a warning signal and may warn a user through an output device.

Figure 17:
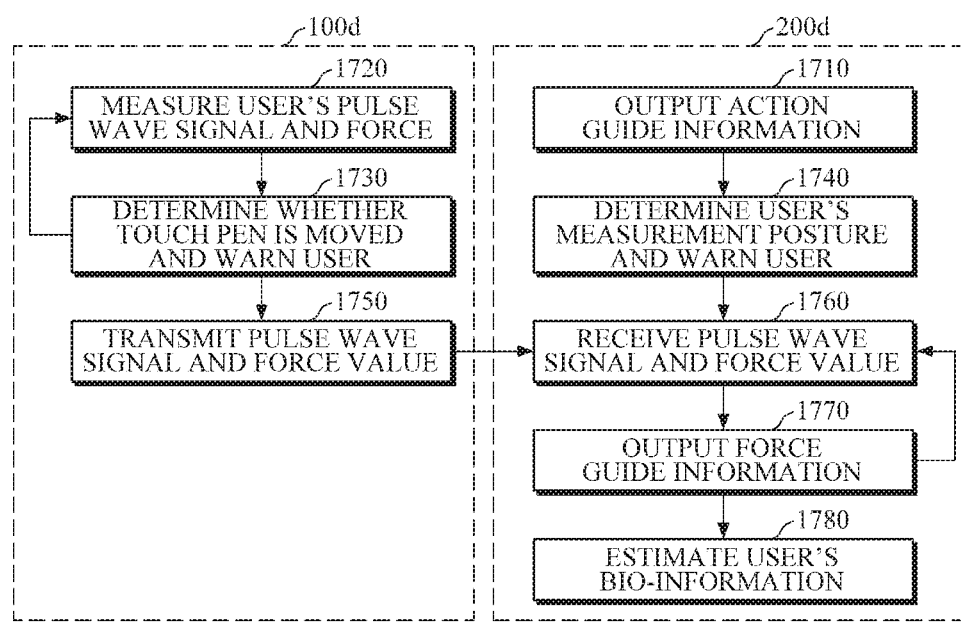
FIG. 17 is a flowchart illustrating a method of measuring bio-information according to still another embodiment.

FIG. 17 is a flowchart illustrating a method of measuring bio-information according to still another embodiment of the present disclosure. The method of measuring bio-information of FIG. 17 may be performed by the apparatus 10d for measuring bio-information of FIG. 13.

Referring to FIG. 17, when a specific event occurs, such as an instruction for measuring blood pressure and the like, the electronic device 200d may generate action guide information for guiding a user's action to measure a user's pulse wave signal by using the touch pen 100d, and may output the generated action guide information through an output device in operation 1710.

When a user places the touch pen 100d on a touch screen of the electronic device 200d according to the action guide information and touches the pulse wave sensor with a finger, the touch pen 100d may measure one or more pulse wave signals and a pressing force of the finger pressing the touch pen 100d in operation 1720.

While the touch pen 100d measures the pulse wave signals, the electronic device 200d may measure acceleration of the touch pen 100d, and may determine whether the touch pen 100d is moved based on the measured acceleration value. Based on determining that the touch pen 100d is moved, the electronic device 200d may generate a warning signal and may warn the user through an output device in operation 1730.

While the touch pen 100d measures the pulse wave signals, the electronic device 200d may determine whether a user's measurement posture is appropriate, and based on determining that user's measurement posture is inappropriate, the electronic device 200d may generate a warning signal and may warn the user through an output device in operation 1740.

The touch pen 100d may transmit the measured pulse wave signals and force value to the electronic device 200d in operation 1750, and the electronic device 200d may receive the pulse wave signals and the force value from the touch pen 100d in operation 1760. In this case, the touch pen 100d and the electronic device 200d may communicate with each other using various communication techniques described above.

Based on the received force value, the electronic device 200d may generate force guide information for guiding a force to be increased or decreased by the user for the pulse wave sensor of the touch pen 100d while the touch pen 100d measures the pulse wave signals, and may provide the force guide information for the user through an output device in operation 1770.

The electronic device 200d may estimate the user's bio-information based on the pulse wave signals, received from the touch pen 100d, and the force value in operation 1780.

Further, in an embodiment, regarding operation 1730, the touch pen 100d may simply measure only acceleration of the touch pen 100d, and the electronic device 200d may determine whether the touch pen 100d is moved and may generate a warning signal. In this case, the touch pen 100d may transmit the measured acceleration value to the electronic device 200d, and the electronic device 200d may receive the acceleration value from the touch pen 100d. Further, the electronic device 200d may determine whether the touch pen 100d is moved based on the received acceleration value, and upon determining that the touch pen 100d is moved, the electronic device 200d may generate a warning signal and may warn a user through an output device.

The present disclosure can be realized as computer-readable code written on a non-transitory computer-readable recording medium. Code and code segments for realizing the present disclosure can be deduced by computer programmers of ordinary skill in the art. The computer-readable recording medium may be any type of recording device in which data is stored in a computer-readable manner. Examples of the computer-readable medium include a read-only memory (ROM), a random access memory (RAM), a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

The present disclosure has been described herein with regard to preferred embodiments. However, it will be obvious to those skilled in the art that various modifications can be made without departing from the gist of the disclosure. Therefore, it is to be understood that that the scope of the disclosure is not limited to the above-mentioned embodiments, but is intended to include various modifications and equivalents included within the spirit and scope of the appended claims.

What is claimed is:

1. An electronic device, comprising:
a touch screen;
a communication interface configured to receive, from a touch pen, a pulse wave signal of a user which is measured from a finger of the user by the touch pen while the touch pen is placed on the touch screen; and
a processor configured to:
determine whether a measurement posture of the user is appropriate based on whether the finger touches the touch screen; and
in response to determining that the user's measurement posture is appropriate, estimate bio-information of the user based on the received pulse wave signal.

2. The electronic device of claim 1, wherein the processor is configured to, in response to the finger touching the touch screen, determine that the user's measurement posture is inappropriate.

3. The electronic device of claim 1, wherein:
the communication interface is configured to receive, from the touch pen, a force value of the finger pressing the touch pen while the touch pen is placed on the touch screen; and
the processor is configured to estimate the user's bio-information based on the received force value and the pulse wave signal.

4. The electronic device of claim 3, wherein the processor is configured to:
based on the received force value, generate force guide information for guiding a force of the finger pressing the touch pen to be increased or decreased by the user while the touch pen measures the pulse wave signal; and
provide the generated force guide information to the user.

5. The electronic device of claim 1, wherein the processor is configured to display a touch pen position guideline, indicating a position to place the touch pen, in a portion of the touch screen.

6. The electronic device of claim 1, wherein:
the communication interface is configured to receive, from the touch pen, an acceleration value of the touch pen which is measured while the touch pen is placed on the touch screen; and
the processor is configured to:
determine whether the touch pen is moved based on the received acceleration value of the touch pen; and
in response to determining that the touch pen is moved, generate a warning signal.

7. The electronic device of claim 1, further comprising a force sensor configured to measure a pressing force of the finger pressing the touch pen while the touch pen is placed on the touch screen.

8. The electronic device of claim 1, wherein the pulse wave signal is a Photoplethysmogram (PPG) signal.

9. The electronic device of claim 1, wherein the bio-information is blood pressure.

10. An apparatus for measuring bio-information, the apparatus comprising: a touch pen comprising:
a pulse wave sensor configured to, in response to a touch of a finger of a user while the touch pen is placed on a touch screen of an electronic device, measure a pulse wave signal of the user from the finger of the user; and
a first communication interface configured to transmit the measured pulse wave signal to the electronic device; and
the electronic device comprising:
a touch screen;
a second communication interface configured to receive the pulse wave signal from the touch pen; and
a processor configured to:
determine whether a measurement posture of the user is appropriate based on whether the finger touches the touch screen; and
in response to determining that the user's measurement posture is appropriate, estimate bio-information of the user based on the received pulse wave signal.

11. The apparatus of claim 10, wherein the touch pen further comprises a force sensor configured to measure a pressing force of the finger pressing the touch pen while the touch pen is placed on the touch screen of the electronic device.

12. The apparatus of claim 10, wherein the electronic device further comprises a force sensor configured to measure a pressing force of the finger pressing the touch pen while the touch pen is placed on the touch screen of the electronic device.

13. The apparatus of claim 10, wherein the touch pen further comprises an acceleration sensor configured to measure acceleration of the touch pen while the touch pen is placed on the touch screen of the electronic device.

14. The apparatus of claim 10, wherein the processor is configured to display a touch pen position guideline, indicating a position to place the touch pen, in a portion of the touch screen.

15. A method of measuring bio-information by an electronic device having a touch screen, the method comprising:
receiving, from a touch pen, a pulse wave signal of a user which is measured from a finger of the user by the touch pen while the touch pen is placed on the touch screen;
determining whether a measurement posture of the user is appropriate based on whether the finger of the user touches the touch screen; and
in response to determining that the user's measurement posture is appropriate, estimating bio-information of the user based on the received pulse wave signal.

16. The method of claim 15, wherein the determining whether the user's measurement posture is appropriate comprises, in response to the finger touching the touch screen, determining that the user's measurement posture is inappropriate.

17. The method of claim 15, further comprising:
receiving, from the touch pen, a force value of the finger pressing the touch pen while the touch pen is placed on the touch screen;
based on the received force value, generating force guide information for guiding a force of the finger pressing the touch pen to be increased or decreased by the user while the touch pen measures the pulse wave signal; and
providing the generated force guide information to the user,
wherein the estimating of the user's bio-information comprises estimating the user's bio-information based on the received force value and pulse wave signal.

18. The method of claim 15, further comprising:
measuring a pressing force of the finger pressing the touch pen while the touch pen is placed on the touch screen;
based on the received force value, generating force guide information for guiding a force of the finger pressing the touch pen to be increased or decreased by the user while the touch pen measures the pulse wave signal; and providing the generated force guide information to the user, wherein the estimating of the user's bio-information comprises estimating the user's bio-information based on the received force value and pulse wave signal.

19. The method of claim 15, further comprising displaying a touch pen position guideline, indicating a position to place the touch pen, in a portion of the touch screen.

20. The method of claim 15, further comprising:
receiving, from the touch pen, an acceleration value of the touch pen which is measured while the touch pen is placed on the touch screen;
determining whether the touch pen is moved based on the received acceleration value of the touch pen; and
in response to determining that the touch pen is moved, generating a warning signal.

* * * * *